United States Patent [19]

Patterson et al.

[11] Patent Number: 4,808,187

[45] Date of Patent: Feb. 28, 1989

[54] TACTILE STIMULUS RECEPTOR FOR A HAND PROSTHESIS

[75] Inventors: Patrick E. Patterson, Ames, Iowa; Judd A. Katz, Montgomery, Ala.

[73] Assignee: Iowa State University Research Foundation, Inc., Ames, Iowa

[21] Appl. No.: 104,067

[22] Filed: Oct. 5, 1987

[51] Int. Cl.$^4$ .............................. A61F 2/70; A61F 2/72
[52] U.S. Cl. .......................................... 623/25; 623/26
[58] Field of Search ........................ 623/24, 25, 26, 63, 623/64

[56] References Cited

U.S. PATENT DOCUMENTS

| | | | |
|---|---|---|---|
| 2,582,234 | 1/1952 | Conzelman, Jr. et al. | 623/26 X |
| 3,464,322 | 9/1969 | Pequignot | 623/66 |
| 3,509,583 | 5/1970 | Fraioli | 623/24 |
| 3,751,733 | 8/1973 | Fletcher et al. | 623/24 |
| 4,094,016 | 6/1978 | Eroyan | 623/24 |
| 4,183,102 | 1/1980 | Guiset | 623/1 |
| 4,623,354 | 11/1986 | Childress et al. | 623/25 |
| 4,650,492 | 3/1987 | Barkhordar et al. | 623/24 |

FOREIGN PATENT DOCUMENTS

| | | | |
|---|---|---|---|
| 2016295 | 10/1971 | Fed. Rep. of Germany | 623/25 |
| 243142 | 5/1969 | U.S.S.R. | 623/25 |

OTHER PUBLICATIONS

"Myo-Electric Control of a Hand Prosthesis" by J. B. Knowles et al., The Journal of Bone & Joint Surgery, vol. 47B, No. 3, Aug. 1965, pp. 16-17.
"A Mechanical Hand With Automatic Proportional Control Of Prehension", Med & Biol. Engineering, vol. 5, 1967, pp. 505-511.
"Sensory Feedback For Powered Limb Prostheses", Medical and Biological Engineering, Mar. 1975, pp. 300-301.
"A Comparison Of Alternative Means Of Providing Sensory Feedback On Upper Limb Prostheses" by G. F. Shannon, Medical and Biological Engineering, May 1976, pp. 289-294.
"Closed-Loop Control in Prosthetic Systems: Historical Perspective" by Dudley S. Childress, Annals of Biomedical Engineering, vol. 8, pp. 293-303, 1980.

Primary Examiner—Ronald L. Frinks
Attorney, Agent, or Firm—Zarley, McKee, Thomte, Voorhees & Sease

[57] ABSTRACT

A means and method for tactile stimulus reception for use with a myoelectric prosthesis includes a pressure transducer positioned on the prosthesis. The pressure transducer senses the level of pressure experienced by the gripping portion of the prosthesis and converts the sensed pressure into a corresponding signal. A pressure stimulus member is positionable upon the user and creates a pressure stimulus proportionally corresponding to the sensed pressure of the pressure transducer by utilizing the signal from the pressure transducer. The pressure stimulus is tactile so that the user can be given direct tactile pressure stimulation corresponding directly with the pressure sensed by the pressure transducer.

15 Claims, 2 Drawing Sheets

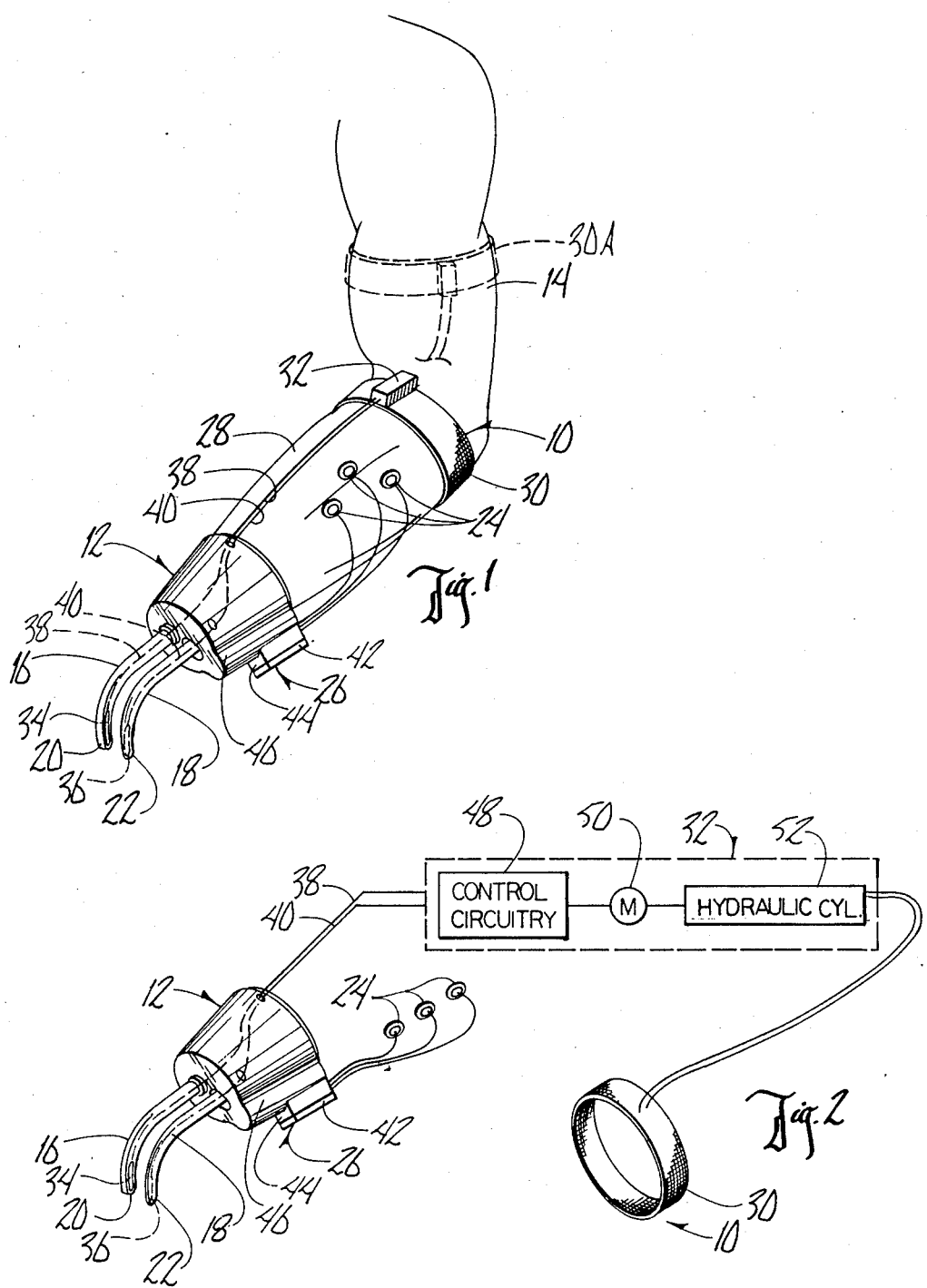

TACTILE STIMULUS RECEPTOR FOR A HAND PROSTHESIS

BACKGROUND OF THE INVENTION a. Field of the Invention

This invention relates to a means and method for stimulus reception for use with a myoelectric prosthesis, and in particular, a means and method of tactile stimulus reception corresponding to pressure sensed by the myoelectric prosthesis.

b. Problems in the Art

Prosthesis technology has significantly advanced to where a prosthesis user can control functioning of the prosthesis by muscular or electro-muscular input. Thus, for example, a prosthetic hand can have gripping fingers which are controlled by slight movement of the forearm muscles of the user, or even by electro-muscular signals sent by the brain intended for the muscles which would normally control the user's natural hand.

These modern prostheses are called myoelectric prostheses. An example of a myoelectric prosthetic hand can be seen in and is described in U.S. Pat. No. 4,623,354, issued Nov. 18, 1986 in the name of inventors Childress et al.

The user can therefore actuate the myoelectric device essentially instantaneously with body and brain functions the same as, or closely similar to, those which would be used with a natural hand. The benefit of such devices is easily understood.

However, problems still exist with such devices. A primary problem with such prostheses as myoelectric hands is that the user has no precise control over gripping force. Through training and repetition, the user can generally learn what input is needed to produce a certain gripping force. However, this is generally not precisely reliable. These problems become particularly acute with regard to handling precise tasks, small objects, fragile or delicate objects, and heavy items. It would therefore be greatly beneficial, and there is a real need in the art, for a system which allows precise control by the user of a myoelectric prosthesis with respect to gripping force. It would further be beneficial to have such a system which can be quickly and easily learned.

It is therefore a principal object of the present invention to present a means and method for tactile stimulus reception for use with a myoelectric prosthesis which improves upon, or solves the problems and deficiencies in the art.

A further object of the present invention is to provide a means and method as above described which allows the user of a myoelectric prosthesis precise and delicate control of gripping of objects.

A further object of the present invention is to provide a means and method as above described which produces a tactile stimulus corresponding to gripping pressure of the myoelectric prosthesis.

A further object of the present invention is to provide a means and method as above described which can be quickly and easily learned, and such learning not being susceptible to unreliability.

Another object of the present invention is to provide a means and method as above described which is economical, efficient, and durable.

These and other objects, features, and advantages of the present invention shall become more apparent with reference to the accompanying specification and claims.

SUMMARY OF THE INVENTION

The present invention presents a means and method for tactile stimulus reception for use with a myoelectric prosthesis. Pressure transducer means are operatively positioned upon the prosthesis. The pressure transducer means creates a signal which corresponds with the amount of pressure sensed and experienced by contact and gripping of an object.

Pressure stimulus means is in turn operatively positioned upon the user. The signal from the pressure transducer means is sent to the pressure stimulus means, which in turn produces a pressure stimulus corresponding to the signal. Therefore, the means and method of the invention present a pressure stimulus proportional to the pressure presented by the prosthesis to allow the user to accurately learn and control gripping pressure.

The pressure stimulus is a tactile stimulus so that the user can "feel" the level of gripping pressure by the prosthesis.

BRIEF DESCRIPTION OF THE DRAWINGS

FIG. 1 is a perspective view of one embodiment of the invention operatively positioned upon a user.

FIG. 2 is a combined schematic and perspective view of the invention isolated from the user and in operative connection to a myoelectric prosthesis device.

DETAILED DESCRIPTION OF THE PREFERRED EMBODIMENT

Figure 3:
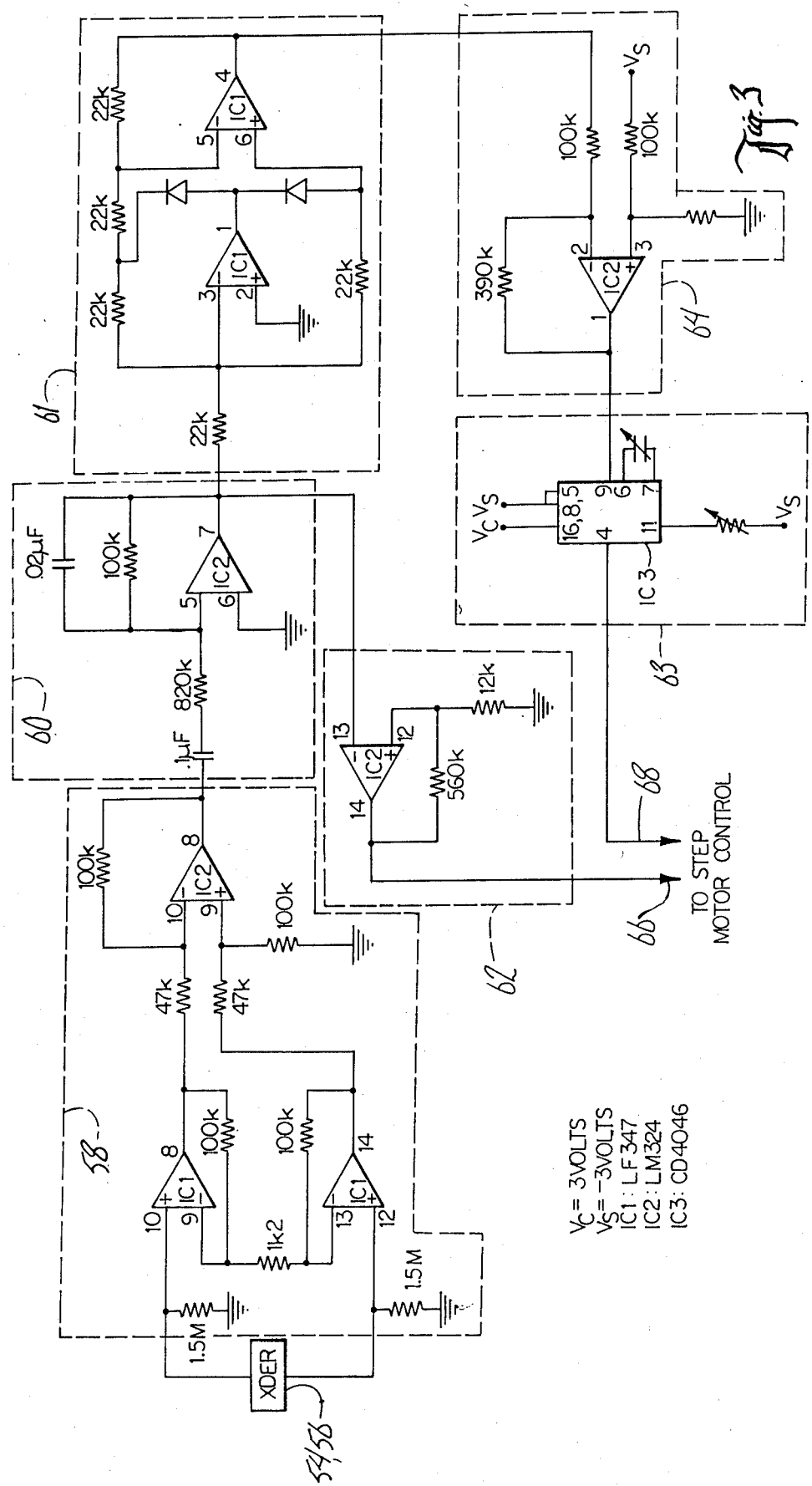
FIG. 3 is an electrical schematic of one embodiment of electrical circuitry for the invention.

In reference to the drawings, and particularly FIG. 1, there is shown a tactile stimulus receptor 10 operatively connected to a myoelectric prosthesis 12, both being operatively positioned upon a user 14.

Myoelectric prosthesis 12 is a myoelectric prosthetic hand such as is known in the art. An example of such a hand can be found at U.S. Pat. No. 4,623,354, to Childress et al., issued Nov. 18, 1986, which is incorporated by reference herein. Myoelectric prosthetic hand 12 includes gripping fingers 16 and 18 having outer ends 20 and 22. At least one of fingers 16 and 18 is movable so that ends 20 and 22 can grippingly come into abutment. The prosthesis 12 also includes electrodes 24 which extend from a control unit 26 to the forearm 28 of user 14. As is known in the art, electrodes 24 sense electro-muscular signals produced by contraction and relaxation of forearm muscles, and convert these signals into electrical signals which are introduced into control unit 26, which in turn opens and closes and grips with the fingers 16 and 18 according to calibrated correlation between relaxation and contraction of the forearm muscles.

As previously described, it is difficult to control precisely the gripping pressure of prosthesis 12, because unlike a natural hand, user 14 has no sensory feedback of the amount of gripping pressure force being exerted by ends 20 and 22 and gripping fingers 16 and 18. Therefore, the tactile stimulus receptor 10 of the present invention accomplishes this advantageous objective.

In the preferred embodiment, a variable pressurizable cuff 30 is positioned in abutment ot and around the user's forearm 28. A control unit 32 is operatively connected to cuff 30 and serves to vary the pressure in cuff 30.

Pressure transducers 34 and 36 are mounted to ends 20 and 22 of gripping fingers 16 and 18 of prosthesis 12.

Pressure transducers 34 and 36 are connected by wires 38 and 40 to control unit 32. Pressure transducers 34 and 36 operate to create an electrical signal corresponding to the level of pressure sensed and experienced in gripping an object. These signals are then processed by control unit 32 which varies the pressure in cuff 30 in proportion to the level of pressure sensing experienced by transducers 34 and 32.

For example, control unit 32 can be designed to incrementally increase pressure in cuff 30 for calibrated increases in sensed pressure by transducers 34 and 36; and conversely, reduce pressure in cuff 30 for decreases in sensed pressure by transducers 34 and 36. Cuff 30 would therefore serve to constrict forearm 28 upon increased pressure, and reduce constriction on forearm 28 upon reduced pressurization. It can therefore be seen that tactile stimulus receptor 10 can function to directly correlate gripping pressure of prosthesis 12 to a tactile stimulus in the form of varying constricting pressure on forearm 28. It is to be understood that cuff 30 could be positioned at various locations on the user's arm. For example, in the case of an above-elbow amputation, cuff 30 could be placed on the upper arm, as shown schematically in FIG. 1, at reference numeral 30A. This closely simulates the working of an actual hand whereby the fingers sense and give information to the brain as to how much gripping pressure is being exerted.

FIG. 2 shows the embodiment of FIG. 1 in more detail. It can be seen that control unit 26 of prosthesis 12 includes control circuitry 42 for receiving the signals from electrodes 24 and instructing hydraulic motor 44 to extend or contract hydraulic cylinder 46 which in turn determines whether gripping fingers 16 and 18 are open or closed, or remain at a certain position. It is to be understood also that control unit 26 can hold gripping fingers 16 and 18 at a selected gripping position.

Control unit 32 of tactile stimulus receptor 10 includes control circuitry 48, hydraulic motor 50, and hydraulic cylinder 52. Control circuitry 48 receives the signals from pressure transducers 34 and 36, processes them to remove extraneous noise, and in turn instructs hydraulic motor 50 to expand or contract hydraulic cylinder 52, which in turn increases or decreases hydraulic pressure in cuff 30. Control unit 32 can also operate to maintain a certain level of cuff pressure in cuff 30.

FIG. 3 sets forth one embodiment of the electrical circuitry of the invention. Pressure transducers 34 and 36 are piezoelectric members 54 and 56. Members 54 and 56 can be made of Kynar piezo film which produces a train of pulses proportional to the mechanical pressure experienced by piezo members 54 and 56. Three integrated circuits (IC1, IC2, and IC3) are utilized in this circuitry. IC1 has an identification number LF347; IC2 is an LM324 chip; and IC3 is a CD4046 chip. These IC's can be purchased through any number of distributors or manufacturers, as is known in the art. Control circuitry 48 first has a section generally designated by reference numeral 58 which is a high common mode rejection ratio (CMRR) differential amplifier which reduces common mode pickup noise in the signal from piezoelectric members 54 and 56, which can be obtained from Pennwalt Corp., 900 1st. Avenue, P. O. Box C, King of Prussia, Pa. 19406. Reference numeral 60 generally designates part of control circuitry 48 which consists of a simple band pass filter to reduce the effects of temperature and low frequency noise. Reference numeral 61 generally indicates a conventional rectifier circuitry, whereas reference numeral 62 designates a Schmidtt trigger component to circuitry 48 which detects the signal polarity of the signal from piezoelectric members 54 and 56. This signal polarity will determine the direction of operation of hydraulic motor 50 which in turn determines whether cuff 30 will be increased in pressure, or decreased in pressure.

Reference numeral 63 generally designates IC3 and attendant components which operate to produce the VCO output to the step motor control, which controls operation of hydraulic motor 50 (see FIG. 2). Reference numeral 64 generally designates a shifting component in circuitry 48 which shifts the signal level down to $V_s$ so that no VCO output results when no pressure changes are detected by piezoelectric members 54 and 56. Thus, outputs 66 and 68 from circuitry 48 are connectable to motor 50 to control its operation.

In the preferred embodiment, motor 50 is a stepper motor which rotates according to the signal polarity of the signal pulses from piezoelectric members 54 and 56. These impulses or signals power the switching mechanism of stepper motor 50 which correspondingly drives a small piston in hydraulic cylinder 52 which exerts hydraulic pressure in the cuff. In the preferred embodiment, $V_c = 3$ volts and $V_s = -3$ volts.

It can therefore be seen that the preferred embodiment achieves at least all the objectives of the invention. Constricting cuff 30 gives the user 14 a sensation of correlated pressure to that which prosthetic hand 12 is exerting on an object. This replication of the pressure sensation of a natural human hand keeps the prosthesis feed-back stimulus in the same mode as a natural human hand.

Tactile stimulus receptor 10 allows a user 14 to learn the use of the myoelectric prosthesis 12 in a shorter period of time. It also enable use of prosthesis 12 without the user 14 having to constantly look at prosthesis 12 for visual cues as to when the object is contacted and how hard the object is gripped. It also allows user 14 to be less dependent upon visually verified gripping of the object, holding of the object, and other maneuvers. It eliminates the problems in the prior art with regard to precise tasks, lifting and holding small, fragile items, or use in gross tasks, for example, lifting and holding heavy objects. The tactile stimulus is pressure on the user's arm in calibrated and proportional correspondence to the pressure on the pressure transducers of the prosthesis. This pressure-to-pressure correlated stimulus allows the invention to produce it advantageous results.

The included preferred embodiment is given by way of example only, and not by way of limitation to the invention, which is solely described by the claims herein. Variations obvious to one skilled in the art will be included within the invention defined by the claims.

What is claimed is:

1. A tactile stimulus receptor for use with a myoelectric prosthesis comprising:

pressure transducer means positioned on the prosthesis for sensing pressure experienced by gripping of an object by the prosthesis, and converting the sensed pressure into a corresponding signal, the pressure transducer means comprising a piezoelectric means which creates electronic impulses proportional to pressure experienced;

pressure stimulus means adapted to be operatively positioned on a user for producing a pressure stimulus corresponding to the pressure sensed by the pressure transducer means, the pressure stimulus means comprising a tactile pressure means adapted to be placed in abutment with the user, and variable pressure generating means operatively connected to the pressure transducer means for producing a variable tactile pressure stimulus proportional to pressure sensed by the pressure transducer means, the tactile pressure means comprising a hydraulically pressurizable cuff member which substantially encircles and abuts the user's truncated limb, the cuff member being variably pressurized.

2. The means of claim 1 wherein the piezoelectric means comprises a piezoelectric film.

3. A tactile stimulus receptor for use with a myoelectric prosthesis comprising:
pressure transducer means positioned on the prosthesis for sensing pressure experienced by gripping of an object by the prosthesis, and converting the sensed pressure into a corresponding signal; and
pressure stimulus means adapted to be operatively positioned on a user for providing a pressure stimulus corresponding to the pressure sensed by the pressure transducer means, the pressure stimulus means comprising a tactile pressure means adapted to be placed in abutment with the user, and variable pressure generating means operatively connected to the pressure transducer means for producing a variable tactile pressure stimulus proportional to pressure sensed by the pressure transducer means, the variable pressure generating means comprising a motor which operates a hydraulic cylinder to produce variable hydraulic pressure according to the operation of the motor.

4. The means of claim 3 wherein the motor comprises a stepper motor which is reversible so as to operate to increase and decrease pressure in the hydraulic cylinder according to instruction.

5. The means of claim 4 wherein the pressure stimulus means further includes an electrical control circuitry means.

6. The means of claim 5 wherein the electrical control circuitry includes a Schmidtt trigger to detect signal polarity for determining the direction in which the stepper motor will turn.

7. The means of claim 5 wherein the electrical control circuitry includes a signal control means which automatically reduces the signal to the pressure stimulus means when no pressure changes are detected so that no pressure stimulus changes are affected.

8. A tactile stimulus receptor for use with a myoelectric prosthesis comprising:
pressure transducer means positioned on the prosthesis for sensing pressure experienced by gripping of an object by the prosthesis, and converting the sensed pressure into a corresponding signal; and
pressure stimulus means adapted to be operatively positioned on a user for producing a pressure stimulus corresponding to the pressure sensed by the pressure transducer means, the pressure stimulus means including an electrical control circuitry means which in turn includes a noise reduction electrical circuitry means for reducing common mode pick-up noise.

9. The means of claim 8 wherein the electrical control circuitry includes a band pass filter for reducing the effects of temperature and low frequency noise.

10. A tactile stimulus receptor for use with a myoelectric prosthesis comprising:
pressure transducer means positioned on the prosthesis for sensing pressure experienced by gripping of an object by the prosthesis, and converting the sensed pressure into a corresponding signal;
pressure stimulus means adapted to be operatively positioned on a user for producing a pressure stimulus corresponding to the pressure sensed by the pressure transducer means;
the pressure stimulus means further including an electrical control circuitry means which includes a signal control means which automatically reduces the signal to the pressure stimulus means when no pressure changes are detected so that no pressure stimulus are affected.

11. The prosthesis device including a tactile stimulus receptor to allow, precise and accurate control of the prosthesis device comprising:
a myoelectrically controlled artificial hand means;
pressure transducer means for position on the myoelectrically controlled artificial hand for sensing pressure experienced by gripping of an object by the artificial hand; and converting the sensed pressure into a corresponding signal, the pressure means comprising a piezoelectric means which creates electronic pulses proportional to pressure experienced;
pressure stimulus means adapted to be operatively positioned on a user for producing a pressure stimulus corresponding to the pressure sensed by the pressure transducer means the pressure stimulus means comprising a hydraulically pressurizable cuff means adaptable to be positioned around the user's truncated limb and a hydraulic cylinder for producing variable hydraulic pressure in response to operation of a motor, which in turn operates in response to the electronic impulses from the piezoelectric means to produce constriction proportional to the release of pressure sensed at the pressure transducer means.

12. A method for tactile stimulus reception for use with a myoelectric prosthesis, comprising the steps of:
positioning a pressure transducer means comprising a piezoelectric film means on the prosthesis for sensing pressure experienced by gripping an object by the prosthesis and converting the sensed pressure into a corresponding electrical signal proportional to pressure experienced; and
positioning a hydraulically pressurizable cuff means on the truncated limb of a user;
utilizing the electrical signals from the pressure transducer means to operate a hydraulic cylinder means to create hydraulic pressure in the cuff means proportional to the pressure experienced at the pressure transducer means, causing the cuff means to constrict the truncated limb, reduce constriction onthe truncated limb, or remain at a certain constriction level according to the pressures experienced at the pressure transducer means, the cuff means producing a precise, accurate sensory stimulus to allow precise and accurate control of the artificial hand.

13. The method of claim 12 comprising the further step of reducing electrical noise to reduce interference with the accurate operation of the artificial hand.

14. The method claim 12 further comprising the step of reducing the effects of temperature to operation of the artificial hand, by including electrical circuitry to suppress the effects of temperature.

15. The method of claim 12 further comprising the step of producing a signal which automatially reduces hydraulic pressure to the cuff means when no pressure changes are detected by the pressure transducer means.

* * * * *